United States Patent [19]  [11] Patent Number: 4,759,510
Singer  [45] Date of Patent: Jul. 26, 1988

[54] UNIVERSAL SCENT-EMITTING TOILET PAPER ROLLER

[76] Inventor: Monroe J. Singer, 2951 Peace River Dr., Harbour Heights, Fla. 33950

[21] Appl. No.: 69,884

[22] Filed: Jul. 6, 1987

[51] Int. Cl.⁴ ............................................. B65H 19/00
[52] U.S. Cl. .................................. 242/55.2; 242/55.55
[58] Field of Search ................... 242/55.2, 55.55, 68.5, 242/73, 118.4, 118.5; 239/52

[56] References Cited

U.S. PATENT DOCUMENTS

| | | | |
|---|---|---|---|
| 2,753,209 | 7/1956 | Klasky | 242/55.55 X |
| 2,801,809 | 8/1957 | Glaner | 242/55.3 |
| 4,068,808 | 1/1978 | King | 242/118.4 |
| 4,428,546 | 1/1984 | Weideman | 242/118.5 |
| 4,497,456 | 2/1985 | Crapser | 242/55.55 |

Primary Examiner—David Werner
Attorney, Agent, or Firm—Merrill N. Johnson

[57] ABSTRACT

A scent-emitting toilet paper roller designed to fit into any rolled paper dispenser. The roller includes three components molded of thermoplastic material. Two of these components are identical vented hollow closed ended generally cylindrical roller halves, each half containing tongues and slots which permit the two roller halves to be axially slidably joined together. The third thermoplastic component is a helical coiled spring designed to fit inside the joined together roller halves and urge the two halves into their maximum axially extended position. A recessed truncated conical projection axially centered on the closed end of each roller half fits the assembled roller into any rolled paper dispenser. A quantity of scent-emitting pellets are contained within the hollow interior of the joined together roller halves to be tumbled about as the roller is rotated by the removal of paper, thus causing scent to be emitted into the atmosphere through vents in the roller.

9 Claims, 1 Drawing Sheet

UNIVERSAL SCENT-EMITTING TOILET PAPER ROLLER

BACKGROUND OF THE INVENTION

My invention lies in the field of bathroom toilet paper roll holders and also bathroom dispensers which emit a pleasant scent into the atmosphere.

Most prior bathroom tissue dispensers carry the roll of toilet paper on a removable and rotatable roller having opposite ends of reduced size held between a pair of spaced apart brackets mounted to extend outwardly from the wall adjacent the commode. The roller must be removed and then reinserted in order to replenish an empty roll of tissue. Another type of dispenser employs a bent wire bracket forming tongs or pinchers that grip the opposite ends of a cylindrical roller when the tongs are forced apart and the roller and its roll of paper are squeezed between the pronged ends of the dispenser. Most commonly, the roller consists of two separate halves of different diameters which fit together, telescoping axially one within the other and held apart by an internal helical spring. Manufacturers of this type of roller must produce and inventory the two roller halves of different diameters, thus increasing the ultimate cost of such rollers.

In order to create a sanitary and pleasant atmosphere in the lavatories of homes, schools, office building, factories, hotels and public facilities, various complicated and often costly devices have been used. Some of these devices are electrically operated, some require manual operation, and some merely evaporate. All require an expensive receptacle, skilled installation and constant monitoring of the supply of scent producing material to attain satisfactory results. All such devices have been cost prohibitive for low fixed income families.

SUMMARY OF THE INVENTION

Having in mind the need for a universal inexpensive toilet paper roller which emits a pleasant scent especially when the toilet paper is used, my invention consists of a toilet tissue roller designed to fit into any tissue dispenser and which comprises a pair of identical injection molded plastic roller halves, an injection molded plastic helical spring, and a quantity of scent-impregnated pellets housed within the joined together roller halves.

The pair of roller halves are hollow cylinders with one closed end and one open end and designed to mate with each other by axially aligning the open ends of two cylinder halves and inserting the protruding sections of one half into the receiving slots in the other half, so the two halves are axially slidably joined together. Contained within the two joined together roller halves is a molded plastic helical spring having ring-shaped ends which rest in compression against ribs of the two roller halves, thus urging the two roller halves into their maximum axially extended position.

A recessed truncated conical projection which is axially centered on the closed end of each roller half is designed to fit the assembled roller into any roller paper dispenser. A quantity of porous material sized larger than the smallest vent in the assembled roller and impregnated with scent is housed within the hollow assembled roller. As the roller is rotated by the removal of paper, the porous material is tumbled about causing scent to be emitted into the atmosphere.

The use of identical halves to make a whole roller saves considerable time and money in the construction of the production tooling and in the inventory of parts. Additional economies in the manufacture of the individual roller halves can be achieved by constructing an injection mold consisting of one or more identical cavities and injection molding polypropylene in very thin wall sections. By assembling the symmetrical halves using automatic hopper feeders and fillers, rotary table fixtures and computer-programmed robotic mating and then on the same assembly line shrink-wrapping the assembled roller to seal in the fragrance, a very low final cost of my scent-emitting roller permits it to be included as an integral part of the package of several rolls of the product it is to dispense as a free advertised premium, thus bringing my scent-emitting roller within the financial reach of all members of the public.

DETAILED DESCRIPTION OF THE PREFERRED EMBODIMENT

Figure 1:
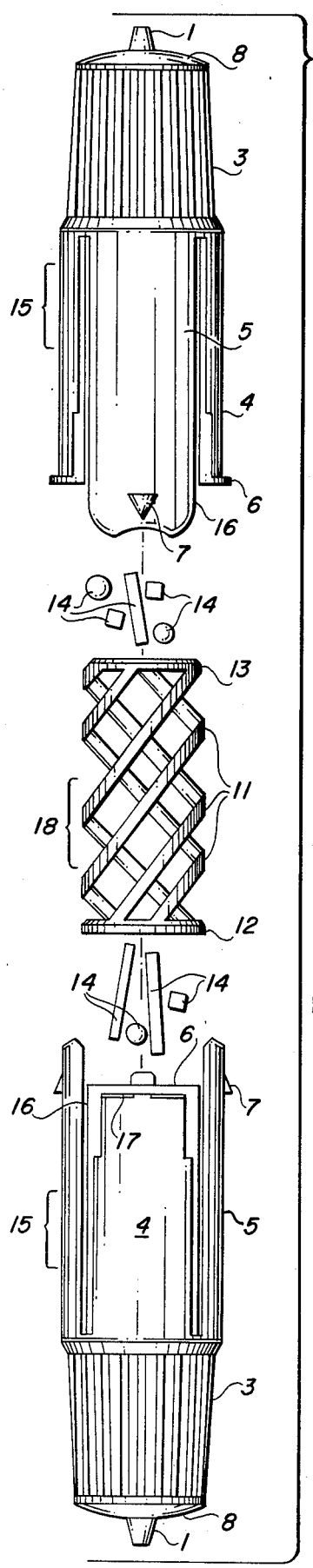
FIG. 1 is an exploded view of a preferred embodiment of my scent-emitting roller showing the two identical roller halves, the helical spring, and several forms of porous scent-emitting pellets.
Figure 3:
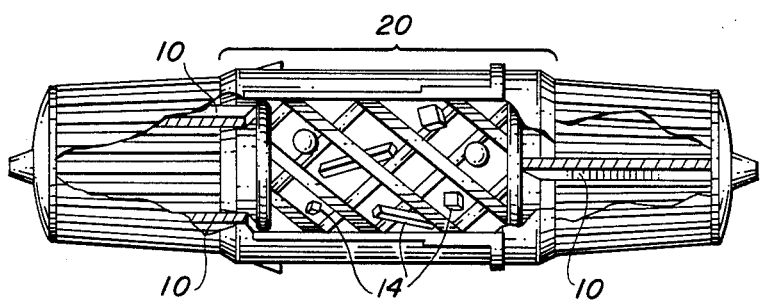
FIG. 3 is an elevational front view partially broken away of my assembled scent-emitting roller whose components are shown in FIG. 1.

Referring first to FIGS. 1 and 3 of the drawings, the assembled roller 20 includes a pair of identical plastic roller halves 15, a compressible plastic helical spring 18 and a quantity of scent-impregnated porous pellets 14.

Roller halves 15 and helical spring 18 are preferably injection molded from polypropylene or other suitable thermoplastic material in very thin walled sections. Pellets 14 are preferably made of micro-porous material sized larger than the largest opening or vent in roller 20 and thoroughly impregnated with a desired slowly evaporating scent.

Figure 2:
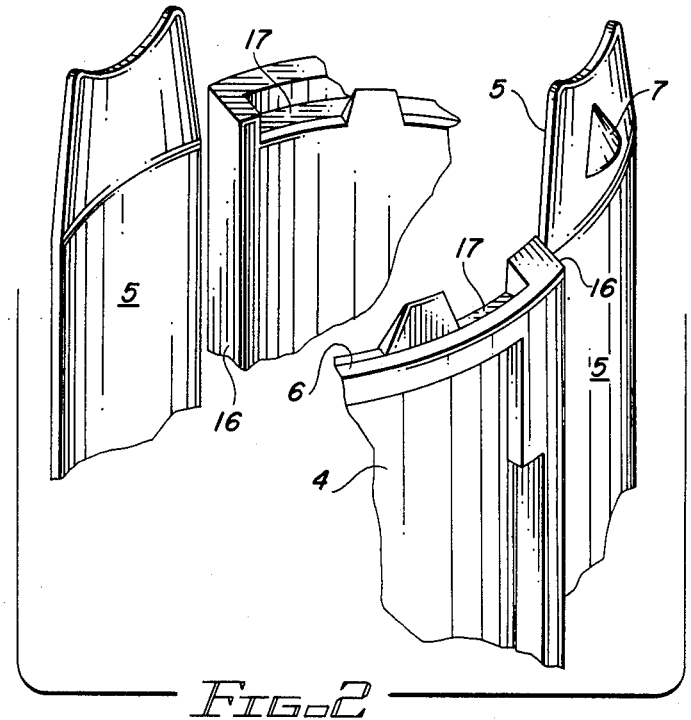
FIG. 2 is a fragmentary detail of the open end of one of the roller halves shown in FIG. 1.

The open end of each roller half 15 is formed by four slightly separated curved walls, namely, a pair of identical short walls 4 separated from a pair of identical tongue-shaped long walls 5 shown in FIGS. 1 and 2. Looking along the axis of the roller half, each wall 4 and 5 subscribes an arc of slightly less than 90° with the four wall separations 16 each subscribing an arc of about 4°. Each of shorter walls 4 has a curved bridging rib 6 forming a curved slot 17 between the rib and the end of wall 4. Slot 17 is sized to accomodate the tongue-shaped long wall 5 of another roller half axially aligned with the first roller half and turned 90° as shown in FIG. 1.

Figure 4:
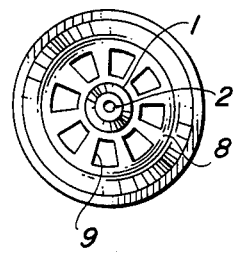
FIG. 4 is an elevational end view of the roller shown in FIGS. 1 and 3.

Each roller half 15 has a truncated conical projection 1 with a recessed aperature 2 axially positioned on its closed end 8 and surrounded by a series of circumferentially spaced vents 9 in the closed end as best shown in FIG. 4. The recessed apertures 2 on the opposite ends of assembled roller 20 are entered by the metal prongs of older style tissue roll dispensers, while the truncated cones 1 fit into the various sized recesses of the newer type built-in-the-wall tissue dispensers. Thus my roller 20 is universal in the sense that it will fit into almost any type of tissue dispenser.

The expansive pressure exerted by helical spring 18 while seated against the inner support ribs 10 within the assembled roller 20 as shown in FIG. 3 adjusts the overall length of roller 20 to the particular dispenser into which the roller is fitted, thus facilitating smooth even withdrawal of sheets of paper from the roll.

As sheets of paper are withdrawn from the roll, irregularities on the circumference of roller 20 such as bridging ribs 6 and wedge-shaped bosses 7 best shown in FIG. 2 cause roller 20 to rotate. This rotation in turn agitates and tumbles the micro-porous absorbent pellets 14 saturated with scent, causing an increase in their emission of vapors. The vapors thus emitted are disbursed into the surrounding atmosphere through end wall vents 9 shown in FIG. 4 and splined dispensing slots 3 shown in FIG. 1 and non-continuous wall separations 16 best shown in FIGS. 1 and 2.

The assembled roller 20 may be compressed and removed from its dispenser in order to replace an exhausted roll of paper since the tongue-shaped walls 5 can slide easily within the slots 17 which are formed by the bridging ribs 6 at the end of the shorter walls 4. Walls 5 and slots 17 have the same radius of curvature. The wedge-shaped boss located on the outer surface of each wall 5 will engage the bridging rib 6 of slot 17 whenever roller 20 is not being compressed, thus limiting its axial expansion when the roller is not fitted into a dispenser.

Figure 5:
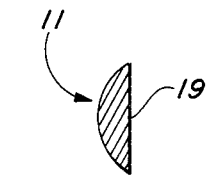
FIG. 5 is a cross-sectional view of one of the helical leads of the helical spring shown in FIGS. 1 and 3.

Helical spring 18 includes several identical helical leads 11 each having in cross-section a flat outer surface 19 and a convex inner surface as shown in FIG. 5. The helix formed by multiple leads 11 is slightly tapered from larger circular ring 12 to a slightly smaller ring 13 as shown in FIG. 1. Spring 18 is sized so that in the assembled roller rings 12 and 13 seat under tension against the ends of inner support ribs 10.

While I have shown and described in detail a preferred embodiment of my scent-emitting paper roller, various changes and modications of the structure will be apparent to those skilled in the art without departing from the spirit of my invention whose scope is limited only by the appended claims.

I claim:

1. A scent-emitting toilet paper roller comprising
   a pair of identical hollow vented generally cylindrical roller halves axially aligned and molded of thermoplastic material, each roller half having two long walls and two shorter walls, each of the two long walls possessing an outwardly projecting restraining boss and each of the two shorter walls possessing a bridging rib that forms a slot, the long walls and their restraining bosses and the shorter walls and their bridging ribs and slots being dimensioned and shaped to mate and join the two axially aligned roller halves together in axially slidable relationship,
   an elongated helical coiled spring separately molded of thermoplastic material having several leads each connected at each end to a ring and designed to fit under compression within the aforesaid joined together roller halves urging the two halves into their maximum axially extended position thus holding the roller firmly within a dispenser until all the paper on the roller has been used,
   a pair of identical truncated conical projections with centrally recessed apertures axially centered on the opposite ends of the joined together roller and designed to fit the roller universally onto any type of dispenser, and
   a plurality of small micro-porous scent-impregnated pellets located within the hollow joined together roller halves.

2. The scent-emitting toilet paper roller set forth in claim 1 which includes irregularities in the form of bridging ribs on the outside of the joined together roller halves which contact the inside of the roll of toilet paper as sheets of the paper are being unrolled and removed from the roll thus causing the joined together roller to rotate and agitate and tumble the scent-impregnated pellets within the roller thereby increasing the vaporization of scent from the porous pellets.

3. The scent-emitting toilet paper roller set forth in claim 1 which includes axially elongated and inwardly projecting inner support ribs within each roller half which, when the joined together roller is rotated, assist in agitating and tumbling the scent-impregnated pellets.

4. The scent-emitting toilet paper roller set forth in claim 1 in which the two roller halves are molded of one type of thermoplastic material and the separate helical spring is molded of a different type of thermoplastic material.

5. The scent-emitting toilet paper roller as set forth in claim 1 in which the helical coiled spring includes on each of its two ends a closed circular ring, one of which rings is larger than the other and said rings being joined together by four identical helical leads.

6. The scent-emitting toilet paper roller set forth in claim 5 in which each of the helical leads has a flat outer surface and a convexly curved inner surface.

7. The scent-emitting toilet paper roller set forth in claim 1 wherein each of the two long walls of each of the two roller halves includes a restraining boss on its outer surface designed to prevent the two roller halves from being completely axially separated by the expansive force of the compressed helical spring, but not preventing axial recompression and slidable adjustment of the two roller halves.

8. A universal scent-emitting rolled paper roller designed to fit into a paper dispenser comprising
   a pair of axially aligned identical hollow vented generally cylindrical roller halves injection molded of thermoplastic material, each roller half having two thin-walled identical long walls circumferentially spaced from two shorter walls having narrow curved slots each sized to mate with one of the long walls and join the two axially aligned roller halves together in axially slidable relationship,
   an elongated helical coiled spring molded of a thermoplastic material with a ring on each end of the coiled spring,
   a pair of identical recessed truncated conical projections axially centered on the opposite ends of the joined together roller designed to fit the roller onto a paper dispenser and
   a plurality of micro-porous vaporizable scent-impregnated pellets housed within the hollow joined together roller halves,
   said roller halves each having a plurality of axially elongated and inwardly projecting inner support ribs which position the helical spring and agitate the scent-impregnated pellets when the roller is rotated about its axis.

9. The scent-emitting rolled paper roller set forth in claim 8 in which each of the two long walls on each of the two roller halves has on its outer surface a wedge-shaped restraining boss having a raised flat back end designed to slip through the slots on the shorter walls as the two axially aligned roller halves mate to form the joined together roller, but whose flat back end limits the axial expansion of the joined together roller halves due to the expansive force of the compressed helical spring, but not preventing the axial recompression and slidable adjustment between the two roller halves.

* * * * *